United States Patent
Smits

(10) Patent No.: US 6,718,211 B2
(45) Date of Patent: Apr. 6, 2004

(54) MEDICAL ELECTRICAL LEAD HAVING BENDING STIFFNESSES WHICH INCREASE IN THE DISTAL DIRECTION

(75) Inventor: Karel F. A. Smits, Munstergeleen (NL)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/947,060

(22) Filed: Sep. 6, 2001

(65) Prior Publication Data

US 2002/0049485 A1 Apr. 25, 2002

Related U.S. Application Data

(62) Division of application No. 09/449,934, filed on Nov. 29, 1999, now Pat. No. 6,556,873.

(51) Int. Cl.$^7$ ................................................ A61N 1/05
(52) U.S. Cl. ................................................ 607/122
(58) Field of Search .......................... 600/372–375, 600/377, 381; 607/115–116, 119, 122, 123, 125–131

(56) References Cited

U.S. PATENT DOCUMENTS

| | | | |
|---|---|---|---|
| 3,825,015 A | 7/1974 | Berkovits | 128/404 |
| 3,865,118 A | 2/1975 | Bures | 128/404 |
| 3,903,897 A | 9/1975 | Woollons et al. | 128/419 PG |
| 3,911,928 A | 10/1975 | Lagergren | 128/418 |
| 3,935,864 A | 2/1976 | Lagergren | 128/418 |
| 3,949,757 A | 4/1976 | Sabel | 128/404 |
| 4,057,067 A | 11/1977 | Lajos | 128/418 |
| 4,154,247 A | 5/1979 | O'Neill | 128/419 P |
| 4,215,703 A | 8/1980 | Willson | 128/772 |
| 4,289,144 A | 9/1981 | Gilman | 128/785 |
| 4,328,812 A | 5/1982 | Ufford et al. | 128/786 |
| 4,393,883 A | 7/1983 | Smyth et al. | 128/785 |
| 4,401,126 A | 8/1983 | Reenstierna | 178/784 |
| 4,401,127 A | 8/1983 | Littleford | 128/786 |
| 4,402,328 A | 9/1983 | Doring | 128/785 |
| 4,402,330 A | 9/1983 | Lindemans | 128/786 |

(List continued on next page.)

OTHER PUBLICATIONS

"Orthogonal Electrogram Sensing", B.N. Goldreyer et al., PACE, vol. 6, Mar.–Apr. 1983, Part II, pp. 464–469.

"Sensing Characteristics of Unipolar and Bipolar Orthogonal Floating Atrial Electrodes: Morphology and Spectral Analysis", A.E. Aubert, et al., PACE, vol. 9, May–Jun. 1986, pp. 343–359.

(List continued on next page.)

*Primary Examiner*—Kennedy Schaetzle
*Assistant Examiner*—Kristen Droesch
(74) *Attorney, Agent, or Firm*—Sirma Wolde-Michael

(57) ABSTRACT

An elongated coronary vein lead having a variable stiffness lead body and most preferably adapted to be advanced into a selected coronary vein for delivering a pacing or defibrillation signal to a predetermined region of a patient's heart, such as the left ventricle is disclosed. A method of pacing and/or defibrillating a patient's heart using the lead is also described. The method of pacing or defibrillating the heart includes advancing the coronary vein lead through both the coronary sinus and into a selected coronary vein of a patient's heart, connecting the lead to an electrical pacing source and applying electrical stimulation to a particular chamber of the patient's heart via the implanted lead. The lead includes a variable stiffness lead body that enhances the ability of the lead to be retained in a coronary vein after the lead has been implanted therein.

6 Claims, 12 Drawing Sheets

U.S. PATENT DOCUMENTS

| | | | | |
|---|---|---|---|---|
| 4,422,460 | A | 12/1983 | Pohndorf | 128/786 |
| 4,444,195 | A | 4/1984 | Gold | 128/642 |
| 4,458,677 | A | 7/1984 | McCorkle, Jr. | 128/786 |
| 4,493,329 | A | 1/1985 | Crawford et al. | 128/786 |
| 4,502,492 | A | 3/1985 | Bornzin | 128/785 |
| 4,567,901 | A | 2/1986 | Harris | 128/786 |
| 4,627,439 | A | 12/1986 | Harris | 128/419 P |
| 4,727,877 | A | 3/1988 | Kallok | 128/419 D |
| 4,882,777 | A | 11/1989 | Narula | 604/281 |
| 4,913,147 | A | 4/1990 | Fahlstrom et al. | 128/419 P |
| 4,930,521 | A | 6/1990 | Metzger et al. | 128/786 |
| 4,962,767 | A | 10/1990 | Brownlee | 128/786 |
| 5,111,811 | A | 5/1992 | Smits | 128/419 D |
| 5,133,422 | A | 7/1992 | Coury et al. | 128/784 |
| 5,144,960 | A | 9/1992 | Mehra et al. | 128/786 |
| 5,172,694 | A | 12/1992 | Flammang et al. | 128/642 |
| 5,273,053 | A | 12/1993 | Pohndorf | 607/132 |
| 5,306,263 | A | 4/1994 | Voda | 604/281 |
| 5,308,342 | A | 5/1994 | Sepetka et al. | 604/282 |
| 5,330,521 | A | 7/1994 | Cohen | 607/122 |
| 5,423,772 | A | 6/1995 | Lurie et al. | 604/282 |
| 5,437,632 | A | 8/1995 | Engelson | 604/53 |
| 5,476,497 | A * | 12/1995 | Mower et al. | 607/122 |
| 5,499,973 | A | 3/1996 | Saab | 604/96 |
| 5,531,685 | A | 7/1996 | Hemmer et al. | 604/95 |
| 5,605,162 | A | 2/1997 | Mirzaee et al. | 128/772 |
| 5,628,778 | A | 5/1997 | Kruse et al. | 607/123 |
| 5,639,276 | A | 6/1997 | Weinstock et al. | 606/129 |
| 5,683,445 | A * | 11/1997 | Swoyer | 607/125 |
| 5,733,496 | A | 3/1998 | Avellanet | 264/470 |
| 5,749,849 | A | 5/1998 | Engelson | 604/53 |
| 5,755,765 | A | 5/1998 | Hyde et al. | 607/122 |
| 5,755,766 | A | 5/1998 | Chastain et al. | 607/122 |
| 5,803,928 | A | 9/1998 | Tockman et al. | 606/191 |
| 5,810,867 | A | 9/1998 | Zarbatany et al. | 606/191 |
| 5,833,604 | A | 11/1998 | Houser et al. | 600/373 |
| 5,855,560 | A | 1/1999 | Idaomi et al. | 600/585 |
| 5,871,531 | A | 2/1999 | Struble | 607/126 |
| 5,897,584 | A | 4/1999 | Herman | 607/122 |
| 5,925,073 | A | 7/1999 | Chastain et al. | 607/122 |
| 5,931,819 | A | 8/1999 | Fariabi | 604/281 |
| 5,931,864 | A | 8/1999 | Chastain et al. | 607/128 |
| 5,935,160 | A | 8/1999 | Auricchio et al. | 607/122 |
| 5,951,597 | A | 9/1999 | Westlund et al. | 607/126 |
| 6,400,992 | B1 * | 6/2002 | Borgersen et al. | 607/122 |

OTHER PUBLICATIONS

"Towards Optimizing the Detection of Atrial Depolarization with Floating Bipolar Electrodes", R.R. Brownlee, PACE, vol. 12, Mar. 1989, pp. 431–442.

"Amplitude and Direction of Atrial Depolarization Using a Multipolar Floating Catheter: Principles for a Single Lead VDD Pacing", D. Flammang, et al., PACE, vol. 14, Jun. 1991, pp. 1040–1048.

"Permanent Pervenous Atrial Sensing and Pacing with a New J–shaped Lead", Smyth et al., Journ. Of Thoracic and Cardiovascular Surgery, 1976, No. 72, pp. 565–570.

"18 Months of Clinical Experience with the Implantable Optimized Sequential Stimulator", H.D. Funke, World Symposium on Cardiac Pacing, $6^{th}$, Montreal, Quebec, 1979: Montreal PaceSymp., 1979, Chapter 16–3.

"A New Lead for Transvenous Atrial Pacing and Sensing", Kruse et al., PACE, Jul.–Aug. 1980, vol. 3, pp. 395–405.

"Three Year Clinical Experience with a New Endocardial Screw–in Lead with Introduction Protection for Use in the Atrium and Ventricle", Bisping et al., PACE, Jul.–Aug. 1980, vol. 3, pp. 424–435.

"Crown of Thorns–Single Pass Lead–Clinical Results", Sowton et al., PACE, Mar.–Apr. 1983, Part II, vol. 6, pp. 470–474.

"Sensing and Pacing with Floating Electrodes in the Right Atrium and Right Atrial Appendage", Aubert et al., Journ. Of Amer. College of Cardiology, 1987, Col. 9, No. 2, pp. 308–315.

"European Multicenter Prospective Follow–Up Study of 1,002 Implants of a Single Lead VDD Pacing System", J.C. Pitts Crick, PACE, 1991, vol. 14, pp. 1742–1744.

"Medtronic Model 2188 Endocardial, Bipolar, Coronary Sinus Pacing Lead: Technical Manual".

* cited by examiner

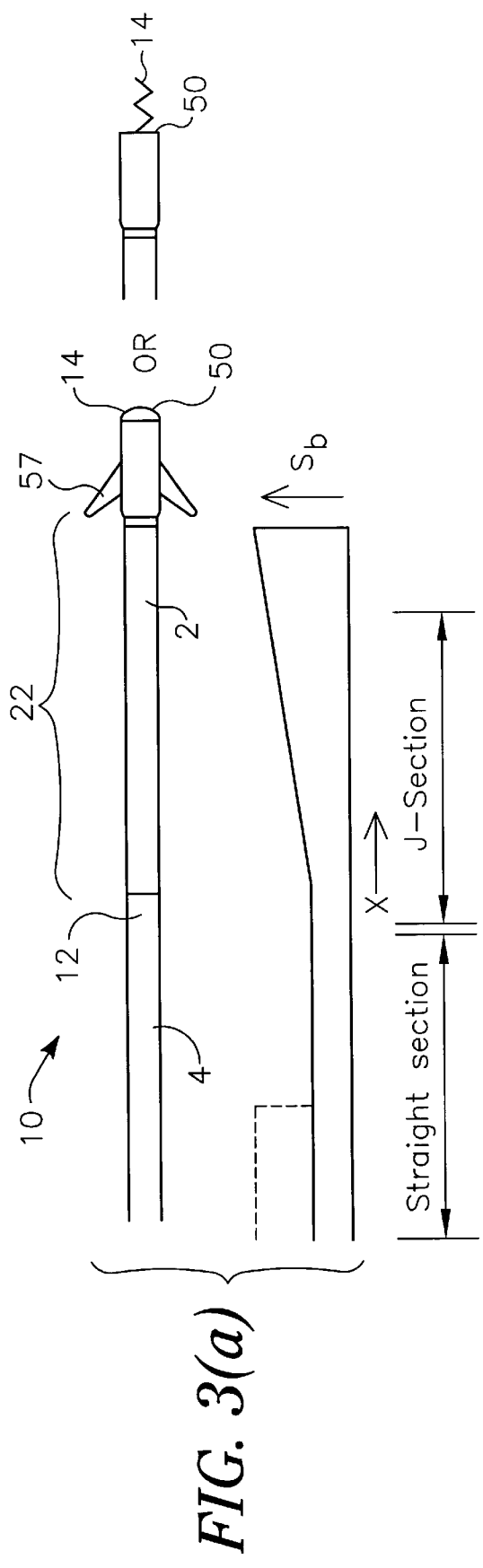
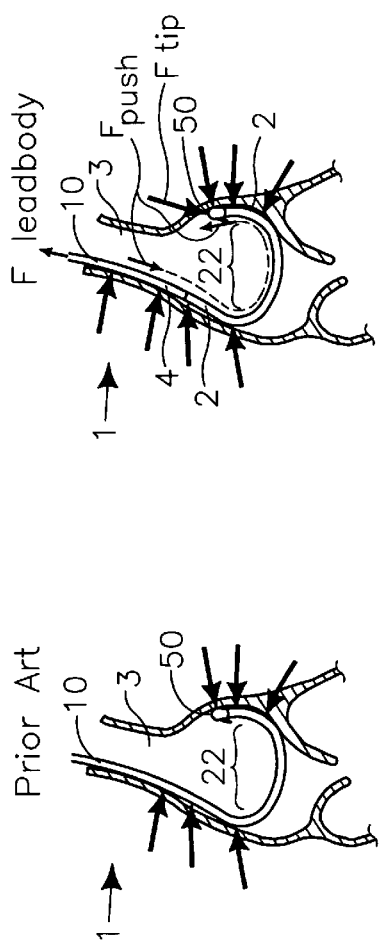
FIG. 3(a)
FIG. 3(b) Prior Art / Conventional Lead
FIG. 3(c) Present Invention

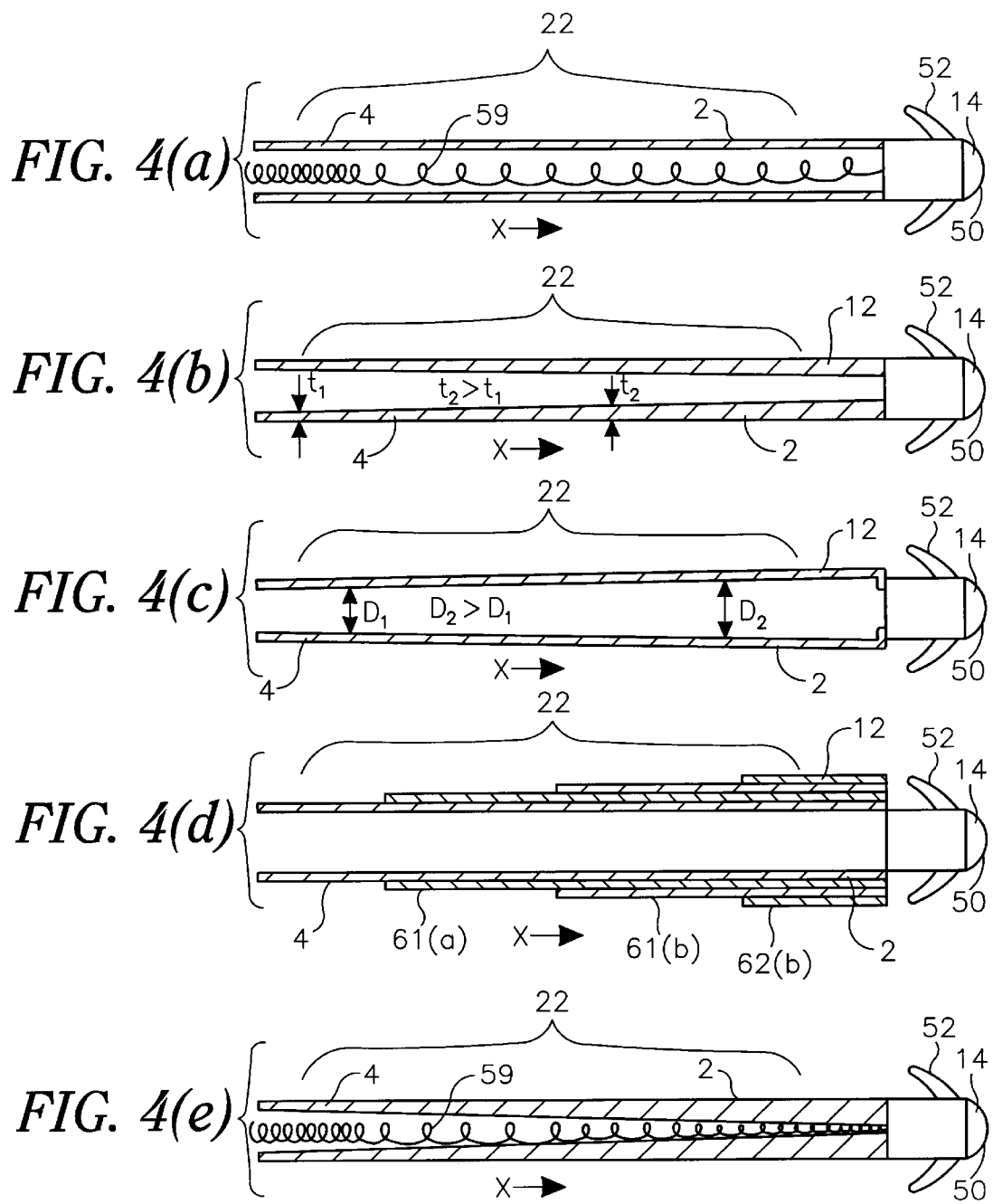

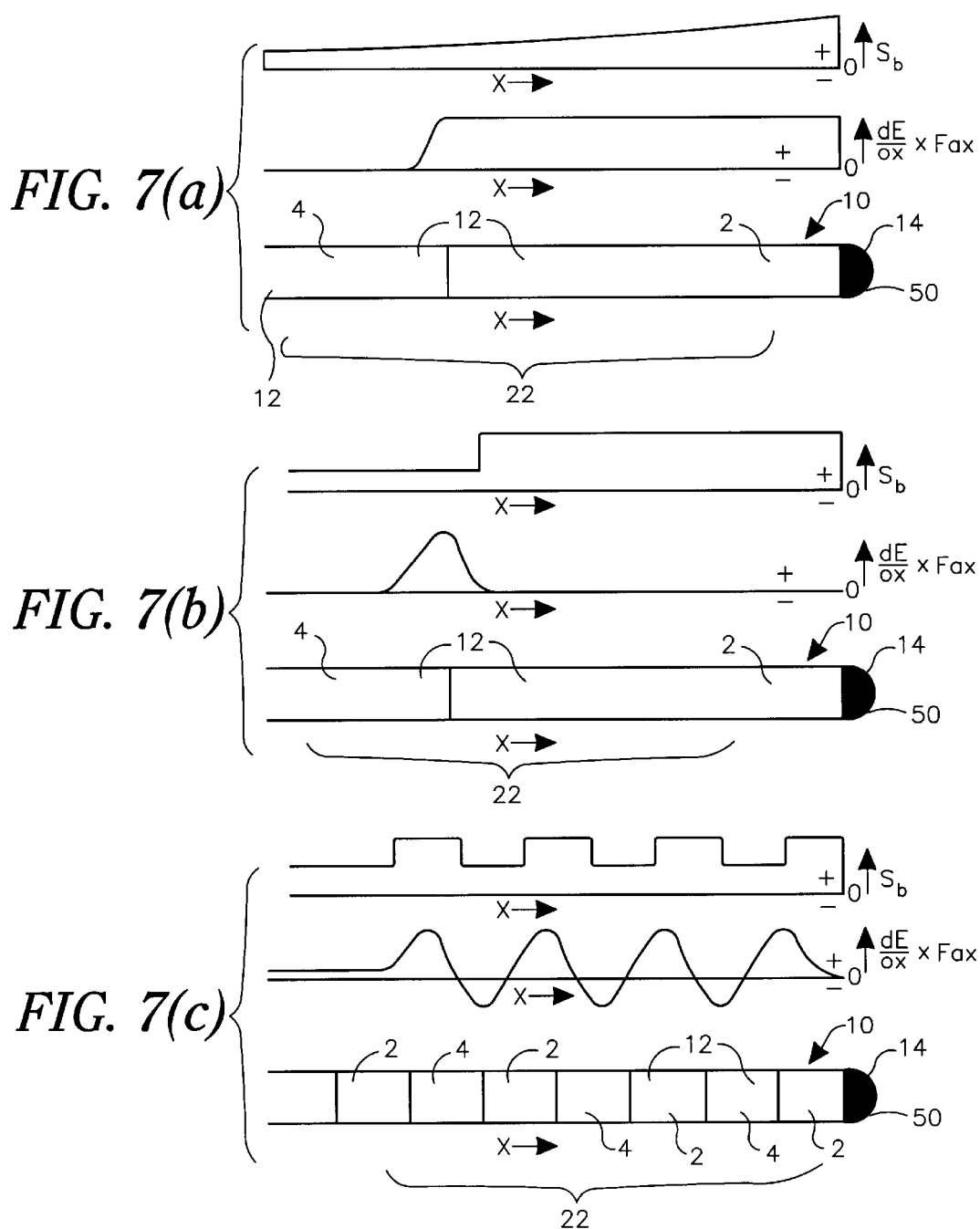

MEDICAL ELECTRICAL LEAD HAVING BENDING STIFFNESSES WHICH INCREASE IN THE DISTAL DIRECTION

This patent application hereby incorporates by reference herein, in its entirety, and is a division of U.S. patent application Ser. No. 09/449,934, filed Nov. 29, 1999 now U.S. Pat. No. 6,556,873 for "Medical Electrical Lead Having Variable Bending Stiffness" to Smits.

FIELD OF THE INVENTION

The present invention relates to pacing and defibrillation medical electrical leads. The present invention also relates to medical electrical leads adapted and configured for implantation within the coronary sinus and coronary veins.

BACKGROUND OF THE INVENTION

Transvenously inserted leads for implantable cardiac pacemakers have conventionally been positioned within the right atrium or right ventricle of the patient's heart for pacing or defibrillating the right atrium and/or right ventricle, respectively. While it is relatively safe to insert a pacing or defibrillation lead and its associated electrodes into the right atrium or right ventricle, there is a reluctance to install a similar lead in the left ventricle because of the possibility of clot formation and resulting stroke.

When a lead is implanted within a patient's circulatory system, there is always the possibility of a thrombus being generated and released. If the lead is positioned in the right atrium or right ventricle, a generated thrombus tends to migrate through the pulmonary artery and is filtered by the patient's lungs. A thrombus generated in the left atrium or left ventricle, however, would pose a danger to the patient due to the possibility of a resulting ischemic episode.

Thus, in those instances where left heart stimulation is desired, it has been a common practice to use an intercostal approach using a myocardial screw-in, positive-fixation lead. The screw-in lead may, however, be traumatic for the patient. There are additional instances when left ventricular pacing is desired, such as during bi-ventricular pacing. In U.S. Pat. No. 4,928,688, Mower describes an arrangement for achieving bi-ventricular pacing in which electrical stimulating pulses are applied via electrodes disposed on a single pacing lead to both the right and left ventricular chambers so as to obtain a coordinated contraction and pumping action of the heart. The '688 patent also discloses a split pacing lead having first and second separate electrodes, wherein the first electrode is preferably introduced through the superior vena cava for pacing the right ventricle and the second electrode is introduced through the coronary sinus for pacing the left ventricle. Other electrode leads which are inserted into the coronary sinus have been described. For example, in U.S. Pat. No. 5,014,696 to Mehra and U.S. Pat. No. 4,932,407 to Williams endocardial defibrillation electrode systems are disclosed.

Still other leads and catheters have been proposed, including those described in the patents listed in Table 1 below.

TABLE 1

| U.S. Pat. No. | Title |
| --- | --- |
| 5,951,597 | Coronary sinus lead having expandable matrix anchor |
| 5,935,160 | Left ventricular access lead for heart failure pacing |
| 5,931,864 | Coronary venous lead having fixation mechanism |

TABLE 1-continued

| U.S. Pat. No. | Title |
| --- | --- |
| 5,931,819 | Guidewire with a variable stiffness distal portion |
| 5,925,073 | Intravenous cardiac lead with wave shaped fixation segment |
| 5,897,584 | Torque transfer device for temporary transvenous endocardial lead |
| 5,871,531 | Medical electrical lead having tapered spiral fixation |
| 5,855,560 | Catheter tip assembly |
| 5,833,604 | Variable stiffness electrophysiology catheter |
| 5,810,867 | Dilation catheter with varied stiffness |
| 5,803,928 | Side access "over the wire" pacing lead |
| 5,755,766 | Open-ended intravenous cardiac lead |
| 5,755,765 | Pacing lead having detachable positioning member |
| 5,749,849 | Variable stiffness balloon catheter |
| 5,733,496 | Electron beam irradiation of catheters to enhance stiffness |
| 5,639,276 | Device for use in right ventricular placement and method for using same |
| 5,628,778 | Single pass medical electrical lead |
| 5,605,162 | Method for using a variable stiffness guidewire |
| 5,531,685 | Steerable variable stiffness device |
| 5,499,973 | Variable stiffness balloon dilatation catheters |
| 5,437,632 | Variable stiffness balloon catheter |
| 5,423,772 | Coronary sinus catheter |
| 5,330,521 | Low resistance implantable electrical leads |
| 5,308,342 | Variable stiffness catheter |
| 5,144,960 | Transvenous defibrillator lead and method of use |
| 5,111,811 | Cardioversion and defibrillation lead system with electrode extension into the Coronary sinus and great vein |
| 4,930,521 | Variable stiffness esophageal catheter |
| 4,215,703 | Variable stiffness guide wire |
| 08/794,175 | Single Pass Medical Electrical Lead |
| 08/794,402 | Single Pass Medical Electrical Lead with Gap Electrodes |

As those skilled in the art will appreciate after having reviewed the specification and drawings hereof, at least some of the devices and methods discussed in the patents of Table 1 may be modified advantageously in accordance with the present invention. All patents listed in Table 1 herein above are hereby incorporated by reference herein, each in its respective entirety.

Prior art coronary vein leads for heart failure applications (i.e., pacing leads) or sudden death applications (i.e., defibrillation leads) generally must be wedged in a coronary vein to obtain a stable mechanical position and to prevent dislodgment. While such an arrangement is generally acceptable for defibrillation leads (which usually must be implanted with the distal tip thereof located near the apex of the heart), such is not the case for heart failure or pacing leads, where more basal stimulation of the heart is generally desired. Basal stimulation of the heart via the coronary vein, however, presents certain difficulties because vein diameters in the basal area of the heart are large and generally do not permit the distal end or tip of a pacing lead to be sufficiently well wedged therein.

Medical electrical leads suitable for implantation within the right atrium and/or right the ventricle are known in the art. Leads having J-shapes imparted to the distal ends thereof are likewise known in the art. Such leads having J-shaped distal ends typically exhibit substantial bending stiffness at the distal thereof, and are most often configured for placement in the right atrium. It is typical that during implantation of such a lead having a J-shaped section at the distal end thereof that, once the lead has been placed within the right atrium, the lead is retracted slightly to impart a positive tip force to the distal end of the lead. Relatively small displacements of the lead in such a manner can result in large variations in the force exerted by the tip of the lead upon the atrial wall. It is therefore not uncommon for the force exerted by the tip to either be excessive or to even become negative, in which event the distal end of the lead is suspended from its own tines or other distally disposed positive fixation device. This, in turn, leads to mechanical instability of the positioning of the distal section of the lead within the right atrium or the right ventricle.

Thus, there exists a need to provide a pacing or defibrillation medical electrical lead which exhibits better mechanical stability following implantation.

SUMMARY OF THE INVENTION

The present invention has certain objects. That is, the present invention provides solutions to one or more problems existing in the prior art. For example, various embodiments of the present invention have one or more of the following objects: (a) providing a medical electrical lead suitable for implantation in the right atrium or right ventricle which is not mechanically unstable once implanted therein; (b) providing a medical electrical lead which exhibits enhanced removability following implantation and fibrosis; (c) providing a medical electrical lead suitable for implantation within the right atrium or right ventricle which requires less time and effort to implant; (d) providing a medical electrical lead which exhibits reduced overall stiffness at the distal end thereof; (e) providing a medical electrical lead, the implantation of which exhibits decreased dependency on the longitudinal position of the lead body thereof in the veins leading to the right atrium or right ventricle; (f) a medical electrical lead wherein small dislodgments occurring near the entrance of the lead in the vein near the anchoring sleeve do not lead to electrode tip dislodgment; and (g) a medical electrical lead wherein the width of the J-shape imparted thereto resulting from implantation within the right atrium or right ventricle may vary according to the distance between the electrode position and the location of the superior vena cava.

Various embodiments of the present invention suitable for implantation within the right atrium or right ventricle possess certain advantages, including one or more of the following: (a) exhibiting multiple lead mechanical stability points which exhibit less dependence on positive fixation mechanisms for proper positioning relative to prior art leads; (b) providing a lead whose retention within the right atrium or right ventricle is less dependent upon the particular shape or diameter of such heart chambers and venous anatomy than prior art leads; (c) providing a lead which permits improved pacing electrode positioning within the right atrium or right ventricle; (d) providing a lead which permits lower pacing thresholds and improved sensing of intracardiac signals; (e) providing a lead which exhibits improved acute and chronic pacing thresholds and sensing characteristics; (f) providing a lead which has no or reduced positive fixation mechanisms attached thereto; (g) providing a lead which may be implanted with an introducer of reduced size; (h) providing a lead which improves chronic lead removability thereof; (i) providing a straight lead which is easier, more reproducible and less expensive to manufacture; (j) providing a lead which exerts a positive electrode tip pressure or force upon the side wall of the right atrium or right ventricle; (k) providing a lead wherein the tip pressure exerted thereby is less dependent on the specific location of the lead body with respect to the venous anatomy leading into the atrium; (l) providing a lead wherein the depth of the placement of the lead tip into the right atrial appendix may be selectively varied; and (m) providing a medical electrical lead having a stiffness which varies as a function of axial distance adapted for specific placement and stability within veins other than the coronary sinus and great cardiac vein, wherein the lead exhibits appropriate distal curvatures and bending stiffnesses required for implantation within the hepatic vein, spinal column, sub-cutaneously, or in other locations within the human body.

Various embodiments of the present invention exhibit one or more of the following features: (a) a distal section of a pacing or defibrillation lead having variable bending stiffness adapted and configured to create a forward driving force of the lead when the variable bending stiffness portion of the distal end of the lead is subjected to a bending moment resulting in sufficient curvature; (b) a pacing or defibrillation lead having in a distal portion thereof a variable bending stiffness section in which the bending stiffness increases with respect to axial distance; (c) a medical electrical lead which owing to variations in bending stiffness along its axial direction imparts a positive tip force or a forward driving force to the lead, and where bending of the lead may preferentially take place along different predetermined bending planes (e.g., three dimensional bending along multiple preferred orientations); (d) a pacing or defibrillation lead wherein variations in bending stiffness are rotationally symmetric; (e) a pacing or defibrillation lead wherein bending stiffness is rotationally asymmetric to permit orientation of one or more electrodes, fixation means, or other lead features relative to the bending plane of a bent or curved section; (f) a pacing or defibrillation lead exhibiting variable stiffness over at least distal portions thereof and which is further characterized in having active or passive fixation features, or no such features, being unipolar or multi-polar, being a pacing or sensing lead, being a defibrillation lead, or having a combination of pacing/sensing and defibrillation capabilities; (g) providing a lead capable of implantation within the right atrium or the right ventricle; (h) providing a lead which may be implanted within the right atrium, right ventricle, the coronary sinus, any of the various and/or one or more of the coronary veins; (i) providing a medical electrical lead having enhanced positive tip pressure exerted thereby to promote the transfer of drugs released from the distal tip or a distal portion thereof into the cardiac wall; (j) providing a medical electrical lead having a side arm extending therefrom in a single pass multi-chamber lead, wherein the side arm is employed to pace or defibrillate the right atrium, and wherein the size of the heart within which the lead is implanted assumes less importance is respect of prior art leads because the lead body may assume a greater range of positions within the superior vena cava; (k) in a single pass multi-chamber lead, a medical electrical lead having a side arm extending therefrom for implantation within the right atrium, which side arm may be more easily located along distal portions of the lead body to facilitate orientation and location of the ventricular electrode; and (l) a medical electrical lead employed in conjunction with a pulled wire for imparting curvature to the distal portion thereof to facilitate handling and prevent the electrode from becoming dislodged during the implantation procedure. Methods of making, using, and implanting a lead of the present invention are also contemplated in the present invention.

These and other objects, features and advantages of the present invention will be readily apparent to those skilled in the art from a review of the following detailed description of the preferred embodiment in conjunction with the accompanying drawings in which like numerals in the several views refer to corresponding parts.

BRIEF DESCRIPTION OF THE DRAWINGS

FIG. 3A illustrates one embodiment of a distal section of a lead body of the present invention and its corresponding bending stiffness profile;

FIG. 3B illustrates a conventional lead implanted within a right atrium;

FIG. 3C illustrates a lead of the present invention implanted within a right atrium;

FIGS. 4A–4E illustrate various means of increasing the being stiffness of the distal section of a lead body in the present invention as a function of axial distance;

FIGS. 7A–7C illustrate schematically several different embodiments of leads of the present invention and their corresponding bending stiffnesses and derivatives of stored mechanical energy with respect to axial distance;

DETAILED DESCRIPTION OF THE PREFERRED EMBODIMENT

Figure 1A:
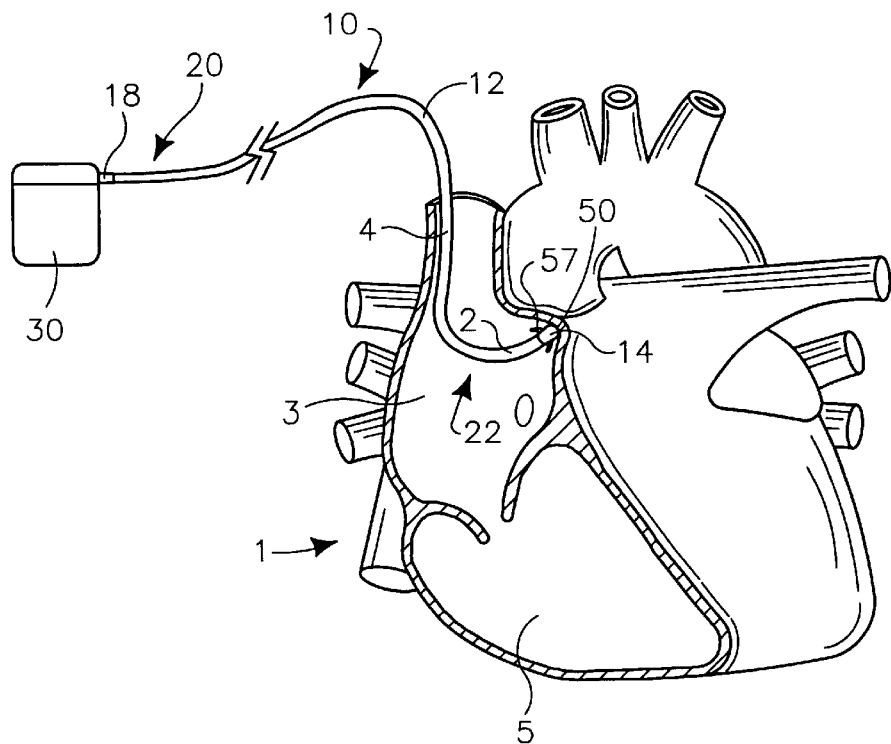
FIGS. 1A and 1B illustrate two different embodiments of the present invention implanted within a human heart.

FIG. 1A shows human heart 1 with medical electrical lead 10 of the present invention implanted therein. Proximal end 20 of medical electrical lead 10 is connected to implantable cardiac stimulator 30 by means of connector or terminal 18. Cardiac stimulator 30 may be a pacemaker, an implantable pulse generator (IPG), an implantable cardiodefibrillator (ICD), a pacer-cardioverter-defibrillator (PCD), or any other type of similar cardiac stimulator well known in the art. Medical electrical lead 10 comprises proximal portion 20, distal portion 22 and lead body 12. Tip 50 is disposed at the distalmost end of lead 10. Electrode 14 may be positioned near tip 50 or at any other suitable location along lead body 12. Tip 50 may also have disposed thereon or adjacent thereto tines 57 or any other positive fixation means such as a helical screw, barb, hook or the like.

As shown in FIG. 1A, lead 10 of the present invention may be implanted in right atrium 3, and preferably displays a J-shaped curve at the distal end thereof upon implantation. Medical electrical lead 10 comprises one or more electrodes 14 disposed thereon for pacing, sensing and/or defibrillating heart 1.

Figure 1B:
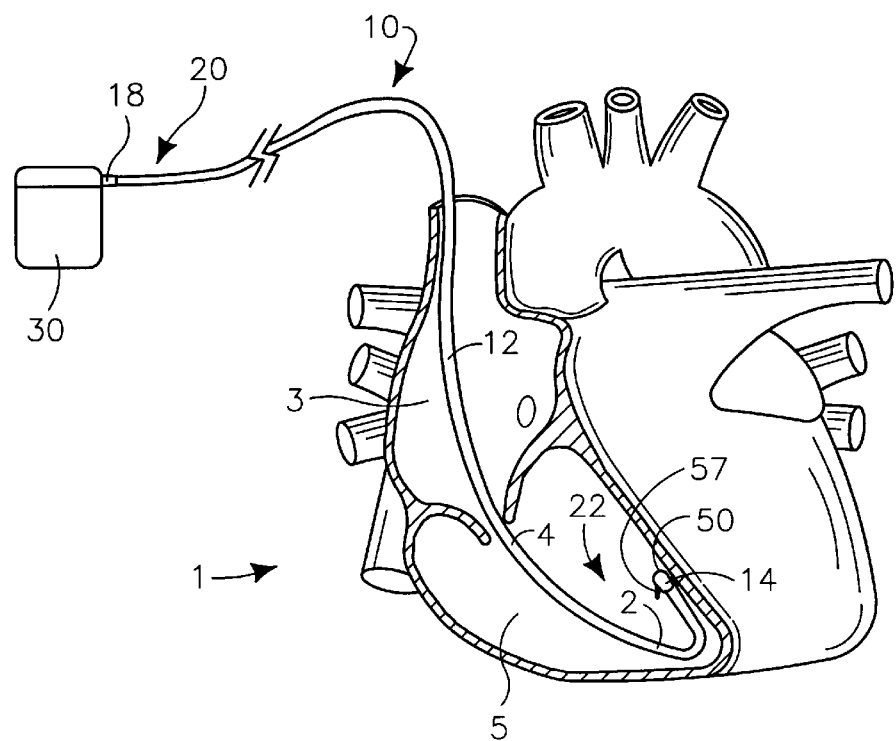

Referring now to FIG. 1B, there is shown human heart 1 with medical electrical lead 10 of the present invention implanted within right ventricle 5. Distal portion 22 of medical electrical lead 10 may similarly exhibit a J-shaped curvature similar to that shown in FIG. 1A. In a preferred embodiment of the present invention distal portion 22 of medical electrical lead 10 does not have a pre-formed J-shaped curve formed therein, but rather prior to implantation assumes a substantially straight configuration which facilitates implantation thereof. In less preferred embodiments of the present invention, however, distal portion 22 of lead 10 may be pre-shaped as desired into, for example, a J-shape.

It is a basic principle of the present invention that distal portion 22 of lead body 12 exhibits increased bending stiffness relative to sections of lead body 12 disposed proximally therefrom. Such a bending stiffness profile as a function of axial distance x has the surprising result of a distally directed force acting upon lead 10 to thereby push lead 10 forwardly or distally, more about which we say below.

Because the bending stiffness of lead 10 increases with axial position x, the amount of energy stored along the curve formed in distal section 22 depends on the position of distal section 22 relative to the curve. When the distal section 22 is moved forward along the curve, the bending stiffness and corresponding stored energy of the portion of section 22 disposed in the curve decreases. That is, a lead which prior to implantation assumes a substantially straight shape and in which distal portion 22 exhibits variable bending stiffness, where the bending stiffness increases in the distal direction upon implantation, exerts a positive tip pressure or force on the walls of atrium 3 or ventricle 5 when it is shaped into a curved J-shape in an attempt to minimize the amount of stored mechanical potential energy. In fact, when lead 10 exhibits a stiffness gradient of about 1 Nmm/radian in distal section 22, a tip force of about 0.1 N results (assuming lead 10 has been bent through a 180° curve over a 15 mm curve radius).

In the present invention, it is contemplated that bending stiffness gradients of distal section 22 of lead 10 range between about 0.05 and about 1.0 Nmm per radian, or between about 0.05 and about 1.5 Nmm per radian. Forces exerted by tip 50 of lead 10 of the present invention may range between about 0.005 N and about 0.1 N. Other ranges of bending stiffness gradients and forces are also contemplated in the present invention, such as stiffness gradients ranging between about 0.1 to about 0.5 Nmm per radian, and forces exerted by distal section 22 ranging between about 0.01 N and about 0.05 N. Other ranges of stiffness gradients and forces are likewise contemplated in the present invention even though not explicitly set forth herein.

Figure 2A:
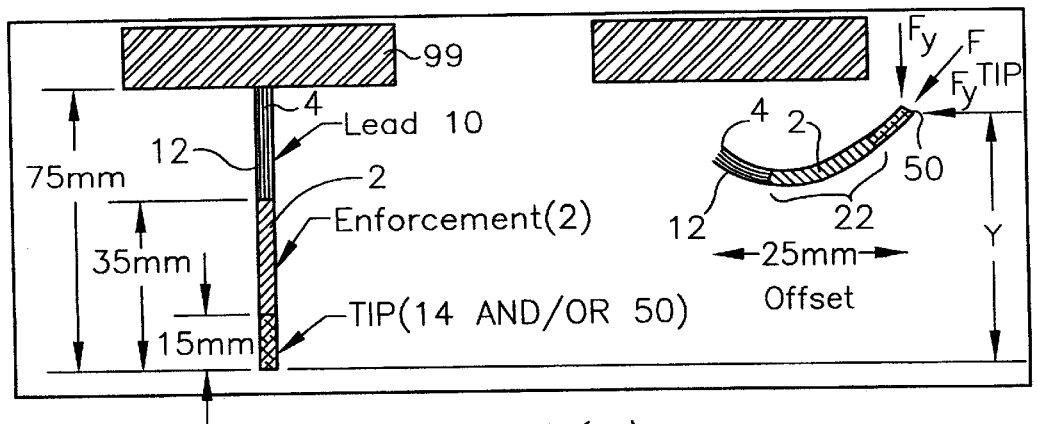
FIG. 2A illustrates parameters employed in modeling one embodiment of the present invention.
Figure 2B:
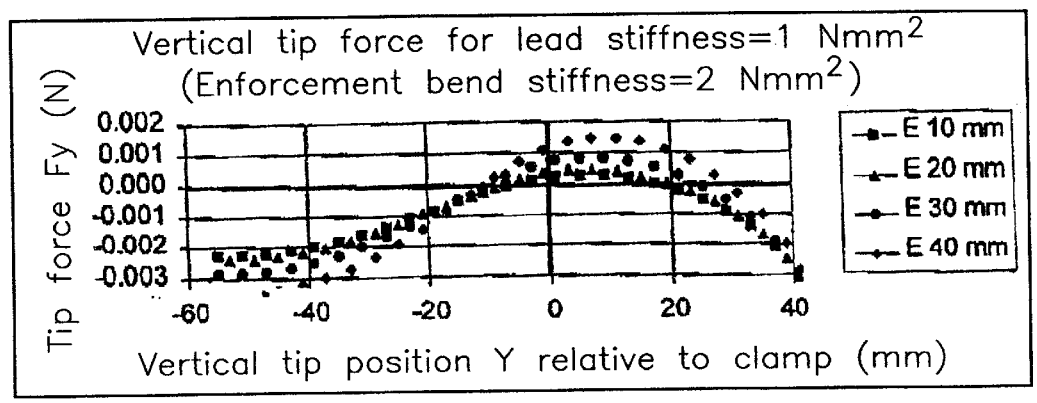
FIG. 2B shows results obtained using the modeling assumptions of FIG. 2A.

Referring now to FIG. 2A, the feasibility of the present invention was tested by means of a computer program. The physical parameters employed in the program are shown in FIG. 2A. The results provided by the program are shown in FIG. 2B.

The lead design parameters employed as inputs to the program included the following: lead 10, rigidly clamped by the "fixed world" 99 at its proximal end, comprised an originally straight lead section 22 which was bent over about 180°. Tip 50 was assumed to form a section about 15 mm long, while reinforced or relatively stiff section 2 had its length varied between about 10 mm and 40 mm. Reinforced section 2 corresponds to relatively stiff section described here below in connection with various embodiments of the present invention. Section 4 of lead body 12 shown in FIG. 2A corresponds to relatively flexible section 4 described below in connection with various embodiments of the present invention. The calculated tip force exerted on distal section 22 of lead 10 having various different lengths of relatively stiff section 2 are shown in FIG. 2B. The calculated tip forces shown in FIG. 2B proved the feasibility of the basic concept of the present invention. A positive force component $F_y$ of the total force F acting on tip 50 is representative for a stable position of tip 50. For a reinforcement (2) of 40 mm length (E40), $F_y$ is positive for vertical tip positions from Y=−10 mm till y=30 mm, corresponding to a range of 40 mm.

Referring now to FIG. 3A, there is shown lead 10 of the present invention having disposed immediately therebelow its corresponding bending stiffness ($S_b$) profile, where the bending stiffness varies as a function of axial distance x. Lead 10 comprises distal portion 22, lead body 12, relatively flexible section 4, relatively stiff section 2, tip 50 and tines 57. Other positive fixation means such as a helical screw, barb, hook, and the like may be disposed on or near tip 50, such as optional tip 50 illustrated to the right of tined tip 57 in FIG. 3A. The bending stiffness profile of lead 10 is shown to increase over the length of that portion of lead 10 which is to have a J-shaped curve upon implantation within right atrium 3 (e.g., at least portions of distal section 22). That is, when initially straight lead 10 is implanted in human heart 1, lead 10 is bent into a J-shaped configuration within right atrium 3 (or right ventricle 5).

Referring now to FIGS. 3B and 3C, there are shown two different leads. FIG. 3B shows conventional lead 10 disposed in right atrium 3 such that distal portion 22 is bent into a J-shape. Superimposed upon the cross-section of lead 10 and heart 1 in FIG. 3B are corresponding force vectors acting upon distal portion 22 of lead 10 in response to the axial forces exerted by lead 10 upon the walls of atrium 3. Note that those force vectors are relatively uniform respecting magnitude.

Contrariwise, the force vectors shown in FIG. 3C acting upon lead 10 are not uniform, and increase in magnitude in the distal direction of lead 10. This feature of the present invention results in the distally directed forward pushing force ($F_{push}$) shown in FIG. 3C which is conteracted by the axial tip force $F_{tip}$ and an axial force on lead body 12, to provide a static equilibrium of forces and moments. As discussed hereinabove, that pushing force is the direct result of the unique bending stiffness profile of distal section 22 of lead body 12.

FIGS. 4A–4E illustrate various means of increasing the bending stiffness of distal section 22 of lead body 10 as a function of axial distance x. FIG. 4A shows coil 59 disposed within lead body 12. The pitch of spring of coil 59 increases in the axial direction x to thereby increase the bending stiffness as one moves towards tip 50 along lead body 12.

FIG. 4B shows another embodiment of the present invention, where the bending stiffness of lead body 12 increases in the distal direction along axial direction x by means of increasing the thickness of the outer covering or layer of lead body 12. Note that an inwardly disposed layer or substrate could also exhibit increasing thickness in the distal direction to achieve the same result. Likewise, a material of uniform thickness but exhibiting changes in its elastic modulii as a function of axial distance x could also be employed to achieve the same result.

FIG. 4C shows another embodiment of the present invention, where an increase in bending stiffness with increasing axial distance x is achieved by increasing the diameter of lead body 12 in the distal direction.

FIG. 4D shows distal portion 22 of lead 10 having successively more layers 61A, 61B and 62B, disposed over outer portions thereof to impart an increase in bending stiffnessess as a function of axial distance x.

FIG. 4E shows one embodiment of the present invention where an increase in bending stiffness with axial distance x is achieved by decreasing the diameter of a coil disposed therein as a function of axial distance x.

It will now become apparent to those skilled in the art, after having read the specification and reviewed the drawings thereof, that many other means of achieving the results of the present invention are possible, where the bending stiffness of lead body 12 in distal section 22 increases in the distal direction.

It is contemplated in the present invention that means of varying the bending stiffness of the distal section of a lead of the present invention other than those described here and above respective FIGS. 4A–4E fall within the scope of the present invention. For example, the material from which lead body 12 is formed may be varied compositionally or otherwise as a function of axial distance x, to thereby effectuate changes in the bending stiffness thereof. The degree to which a polymer forming lead body 12 is cross-linked may be varied as a function of axial distance x. The density of the polymers or other materials employed to form lead body 12 may be varied as a function of axial distance x. The molecular weight of the polymers or other materials from which lead body 12 is formed may be varied as a function of axial distance x. A flexible tubular member containing a shape-memory tube may be included in a lumen extending along a central axis of the lead body, and a control system may then selectively heat portions of the shape-memory tube to change the bending stiffness or shape thereof. The foregoing and other methods of varying the bending stiffness of the distal section of a lead body of the present invention are contemplated in the present invention. See, for example, U.S. Pat. No. 5,437,632 for "Variable stiffness balloon catheter"; U.S. Pat. No. 5,499,973 for "Variable stiffness balloon dilatation catheters"; U.S. Pat. No. 5,531,685 for "Steerable variable stiffness device"; U.S. Pat. No. 5,639,276 for "Device for use in right ventricular placement and method for using same"; U.S. Pat. No. 5,833,604 for "Variable stiffness electrophysiology catheter"; and U.S. Pat. No. 5,733,496 for "Electron beam irradiation of catheters to enhance stiffness", the disclosures of which are hereby incorporated by reference herein, each in its respective entirety.

Figure 5:
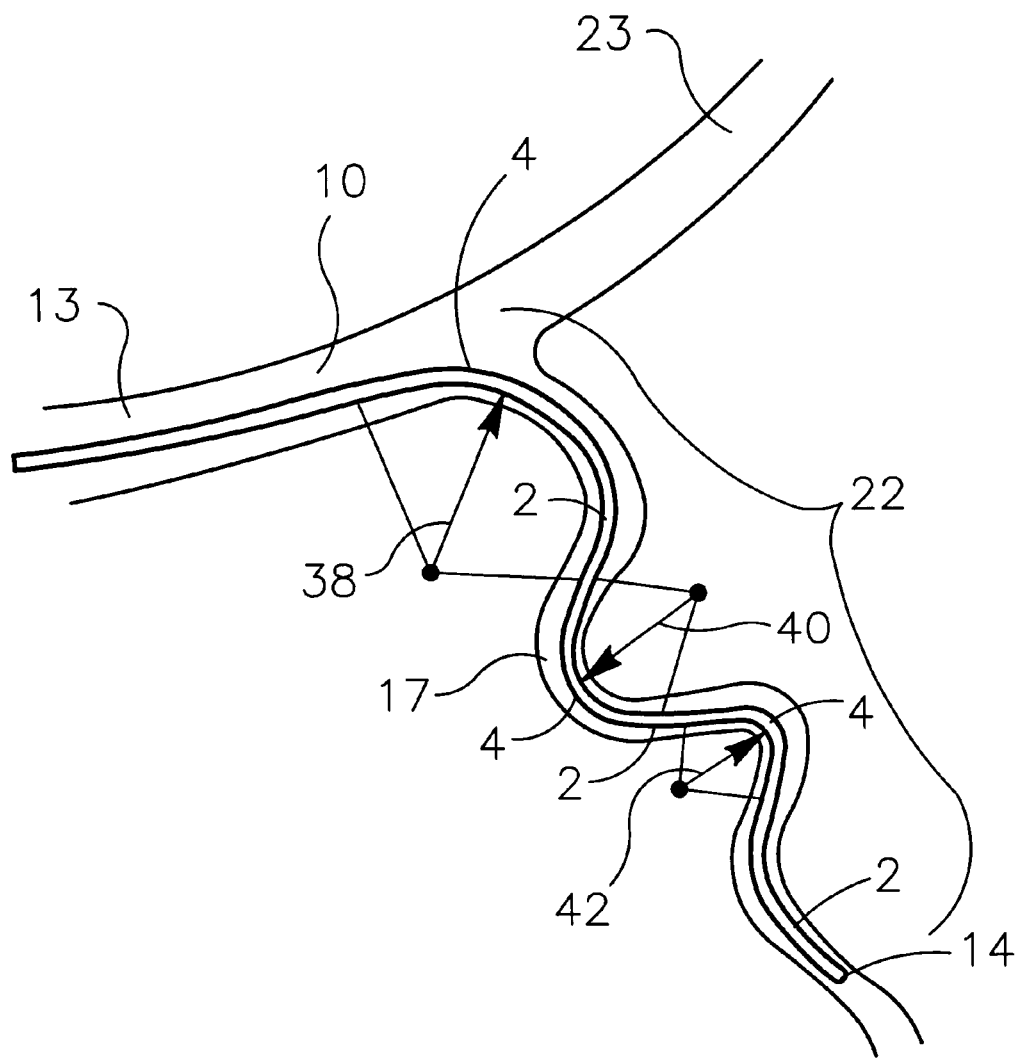
FIG. 5 shows a partial cross-sectional view of a heart having one embodiment of a lead of the present invention disclosed therein.

Referring now to FIG. 5, there is shown a cross-sectional view of lead 10 disposed in, for example, posterior cardiac vein 17 of heart 1 via coronary sinus 13 and great cardiac vein 23. At least portions of distal portion 22 of lead 10 are located in posterior cardiac vein 17. FIG. 5 illustrates how lead 10 must be routed through a series of winding tortuous pathways when implanted in the cardiac veins. Such pathways not only make implantation and placement of lead 10 in desired portions of heart 1 difficult, but also have a tendency to cause prior art leads to be pushed out of the cardiac vein in which they have been located by implantation, further discussion concerning which follows below.

Continuing to refer to FIG. 5, there is shown medical electrical lead 10 of the present invention, which prior to implantation most preferably has a straight distal section 22 and which is adapted for implantation within coronary sinus 13, great cardiac vein 23, or within any other of the left ventricular coronary veins or left atrial veins when appropriately configured and dimensioned. In the present invention, the bending stiffness of distal section 22 of lead 10 is made variable so as to increase or decrease in a predetermined singular or periodic fashion.

Thus, in one embodiment of the present invention distal portion 22 of lead 10 has at least one distalmost stiff section 2 disposed distally of a flexible section 4 located adjacent thereto. That is, lead body 12 may be configured to have at least one stiff section 2 and at least one flexible section 4 located in distal portion 22 thereof. Medical electrical lead 10 of the present invention may additionally have adjacent adjoining portions which alternate between being flexible and being stiff relative to one another. More particularly, the flexibility or stiffness of sections 2 and 4 of lead 10 may be more accurately characterized as having different bending stiffnesses ($S_b$), wherein the ratio of the bending stiffness of the stiff section 2 ($S_{bs}$) is at least 1.5 times that of the bending stiffness of the flexible section 4 ($S_{bf}$). The bending stiffness ratios between more flexible sections 4 and more stiff sections 2 of lead may also exceed about 1.8, about 2, about 2.2, about 2.4, about 2.6, about 2.8, about 3.0, about 4, about 5, about 6, about 7, about 8, about 9, about 10, about 20, about 30, about 40, about 50, about 100 or even greater.

Expressed mathematically, the ratio of bending stiffnesses of stiff sections 2 and flexible sections 4 of lead 10 of the present invention are:

$$1.5 \leq \frac{S_{bs}}{S_{bf}} \leq 100 \qquad \text{(eq. 1)}$$

$$1.5 \leq \frac{S_{bs}}{S_{bf}} \leq 20 \qquad \text{(eq. 2)}$$

$$2 \leq \frac{S_{bs}}{S_{bf}} \leq 10 \qquad \text{(eq. 3)}$$

$$2 \leq \frac{S_{bs}}{S_{bf}} \leq 5 \qquad \text{(eq. 4)}$$

When lead 10 is advanced through coronary sinus 13 into great cardiac vein 23 and then into posterior cardiac vein 17, for example, lead 10 will assume a winding, almost wave-shaped configuration, such that distal portion 22 is curved at the transition between coronary sinus 13 and posterior cardiac vein 17 as well as along the pathway of posterior cardiac vein 17.

It has been discovered that lead 10 will attempt to assume a position with minimal stored mechanical energy after having been implanted within veins 17 and 13. It has further been discovered that flexible sections 4 of lead 10 are most preferably located in those portions of the venous pathway having the curves of smallest radius (and therefore requiring the lowest amounts of stored potential mechanical energy).

Thus, first radius of lead body curvature 36 shown in FIGS. 1A and 1B is most preferably located along those portions of lead 10 which comprise flexible portion 4 of lead body 12. Likewise, second, third and fourth radii of lead body curvatures 38, 40 and 42, respectively, shown in FIG. 5 are likewise located along portions of lead 10 comprising flexible portions 4. Relatively straight portions of lead 10, implanted within human heart 1 in a desired position preferably comprise relatively stiff portions 2 of lead body 12 as shown in FIG. 5.

In the present invention, therefore, moving flexible sections 4 from their locations within first, second, third and fourth curves 38, 40 and 42 requires that an axial force be exerted on lead 10 to advance lead 10 distally (i.e., exertion of a pushing force) or to retract lead 10 (i.e., exertion of a pulling force). Thus, owing to the unique variation of bending stiffness along the length and axial direction x of lead body 12 of lead 10, lead 10, once implanted, has a pronounced tendency to remain implanted and not to become dislodged from the cardiac vein within which it has been implanted.

Figure 6C:
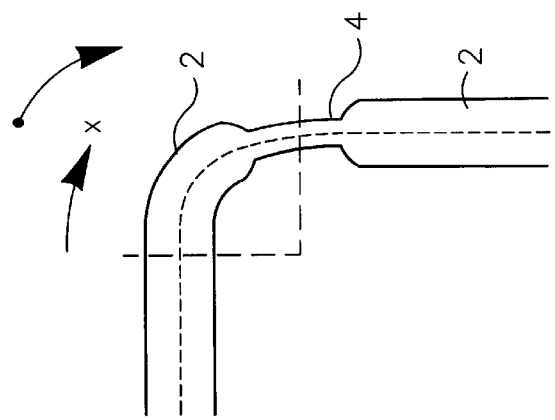
FIGS. 6A–6C illustrate various principles associated with bending stiffness in respect of several embodiments of the present invention.
Figure 6B:
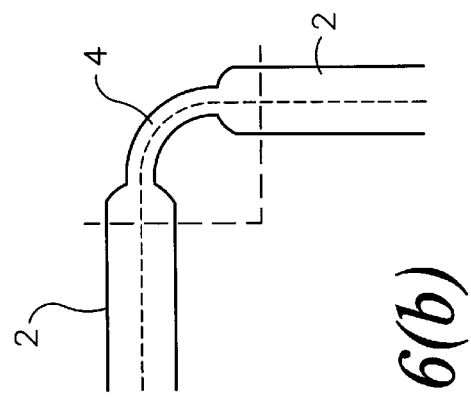
Figure 6A:
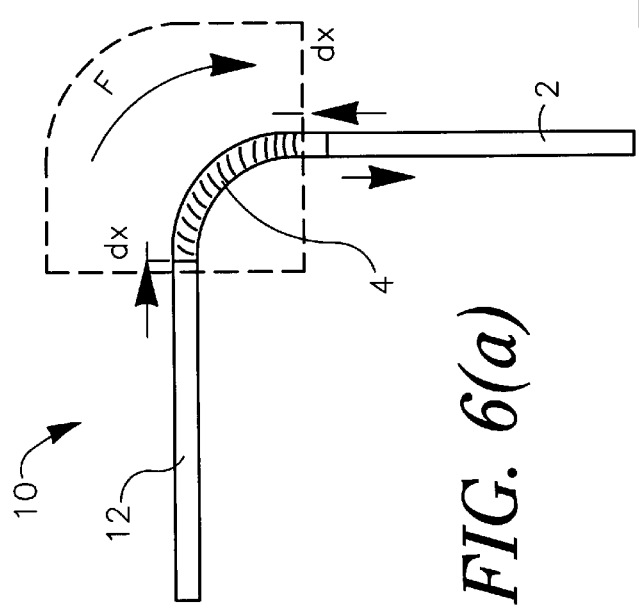

FIGS. 6A–6C illustrate various principles associated with the foregoing discussion concerning FIGS. 1 and 5. The principle of a relatively straight lead having variable bending stiffness as a function of lead position is based on two mechanical laws: (1) a mechanical body subjected to an external load or deformation assumes a shape which minimizes the potential mechanical energy stored in that body; and (2) variation of the stored potential energy in a body with displacement of the body results from an external force acting thereon. The external force (F) equals the derivative of energy (E) with respect to displacement (x) as shown below:

$$F = \frac{dE}{dx} \qquad \text{(eq. 5)}$$

$$\frac{dE}{dx} = \frac{\varphi_b \cdot R_b}{R_b} \cdot \frac{dS_b}{dx} = \varphi_b \cdot \frac{dS_b}{dx} \qquad \text{(eq. 6)}$$

where $S_b$=bending stiffness, $R_b$=bending radius and $\varphi_b$ is the bend angle.

In FIG. 6A the additional energy stored in curved flexible section 4 of lead body 12 is defined by the force F required to displace lead 12 into the position shown along with the change in displacement dX. FIGS. 6B and 6C illustrate that the amount of bending energy required to bend lead body 12 through an approximate 90° curvature is greater for the geometry shown in FIG. 6C than is that illustrated in FIG. 6B. This is because stiff section 2 is located in the curved section of lead body 12 is FIG. 6C. Greater bending energy is therefore required to bend lead body 12 into the configuration shown in FIG. 6C than the configuration shown in FIG. 6B, where flexible section 4 is disposed along most of the curved section. In other words, the lead configuration shown in FIG. 6B is mechanically more stable than is the configuration shown in FIG. 6C because the configuration of FIG. 6C achieves a lower stored mechanical energy level.

Applying the law of minimum stored mechanical energy to the distal section of lead 10, we can draw the following conclusions. When lead 10 is implanted in coronary sinus 13 and great cardiac vein 23, mechanical energy is stored in those curved sections of lead 10 which are located in the transition from coronary sinus 13 to coronary vein 23 or 17. Such stored mechanical energy is proportional to the stiffness of lead 10 and the length being curved, as well as to the curvature (which is the inverse of the bending radius). Assume that the curvature is determined mainly by the venous anatomy, that the angle or curvature is about 90° and that the bend radius is about 5 mm. Such a curve will be maintained by forces acting on both sides of the lead body. The energy stored in lead body 12 is proportional to the average stiffness in the curved section.

Because the stiffness in the curved section varies with the position of the lead along the curve, the average stiffness of the lead body disposed in the curve will change if the lead is moved along the curve or the curve is moved with respect to the lead. Thus, axial displacement x of lead 10 along the curve defined by the venous anatomy results in a change in stored mechanical energy. If a lead of the present invention has been implanted within the venous anatomy of a patient properly, additional energy from an external source (e.g., a physician pulling or pushing the lead along the axial direction x) will have to be provided to displace lead 10 from its preferred minimum stored mechanical energy position.

It has been discovered that it is preferred to locate the most flexible section of the lead in those portions of the venous anatomy which exhibit the greatest curvature (or maximum bend radii). In such a configuration, the stiffness of lead 10 increases both proximally and distally with respect to the flexible section disposed in the curved section, and thus the stored energy of the lead body will become greater if the lead is moved either distally or proximally, or the venous anatomy moves with respect to the lead either distally or proximally. Stored mechanical energy is maintained at a minimum when the flexible section remains in the center of the curve. This results in a stable mechanical equilibrium, which in turn requires that external force of sufficient magnitude be exerted on lead 10 to move it distally or proximally from its minimum stored mechanical energy position.

In accordance with some embodiments of the present invention, lead 10 may be configured to have one relatively stiff portion 2 adjoining a relatively flexible portion 4, or may have a series of alternating relatively stiff portions 2 and relatively flexible sections 4. The bending stiffness of adjoining sections may increase or decrease in step-wise fashion, or may increase or decrease monotonically, exponentially or logrithmically. The respective lengths of relatively stiff portions 2 and relatively flexible portions 4 may also be varied according to the particular venous anatomy in which lead 10 is to be implanted.

In one embodiment of the present invention lead 10 is substantially straight prior to implantation and exhibits variable stiffness in distal portion 22 thereof such that at least one flexible section 4 adjoins proximally disposed and adjacent stiff portion 2 and distally disposed and adjacent stiff section 2, respectively. Such a lead configuration exhibits a bilateral, stable equilibrium (see FIG. 7C).

In another embodiment of the present invention lead 10 has a single stiff section 2 disposed in distal portion 22 which has a relatively flexible section 4 disposed proximally therefrom and adjacent thereto. Such a lead configuration has a unilateral, mechanically stable equilibrium, wherein the bending stiffness junction between sections 2 and 4 of differing stiffness is optimally placed at either end of a curve in a venous anatomy (see FIG. 7B).

FIGS. 7A–7C illustrate the behavior of several selected embodiments of lead 10 of the present invention, where bending stiffness ($S_b$) of lead body 12 is varied as a function of lead axial position x. In each of FIGS. 7A–7C, the upper diagram illustrates bending stiffness $S_b$ as a function of lead axial position x, the middle diagram illustrates the derivative of stored mechanical energy E with respect to axial distance x, (such derivative of stored mechanical energy being proportional to the axial force $F_{ax}$ exerted by the lead), and the lower diagram illustrates a lead structure corresponding to the bending stiffnesses and axial forces illustrated thereabove. In all of FIGS. 7A–7C the distal tip of the lead is positioned at the right side of the diagrams, relatively stiff portions of lead 10 are indicated by numeral 2 and relatively flexible sections of lead 10 are indicated by numeral 4.

Referring now to FIG. 7A, the monotonic increase in bending stiffness begins at the junction between sections 4 and 2 and increases to a maximum at tip 50. Such a configuration results in an axial force ($F_{ax}$) being exerted by lead 10 as shown in the middle diagram. Here, as in other axial force diagrams which follow below, a positive axial force is one which acts to pull the lead in a distal direction, whereas a negative axial force acts to pull a lead in a proximal direction (i.e., out of the vein within which it has been implanted).

Referring now to FIG. 7B, there is shown a lead exhibiting a step-wise jump in bending stiffness which occurs at the junction between sections 2 and 4 thereof. Once distalmost stiff portion 2 has been pushed beyond the venous curve of interest, and flexible section 4 is disposed in such curve, the axial force ($F_{ax}$) exerted by distal portion 22 of lead 10 upon the venous anatomy is again positive and tends to retain the lead in the implanted position unless an axial pulling force operating in the proximal direction is exerted on lead 10 to pull lead 10 around the curve of interest to thereby overcome $F_{ax}$.

FIG. 7C shows lead 10 having a series of contiguous alternating relatively flexible and relatively stiff sections 2 and 4, respectively. Lead 10 shown in FIG. 7C exhibits a number of points of bilateral stability separated by a distance equal to the length of relatively flexible and relatively stiff sections 4 and 2, respectively. Such a lead configuration has the advantage that a tip or electrode thereof may be placed at any of several positions along one or more coronary veins. That is, the embodiment of lead 10 shown in FIG. 7C has a number of different minimum mechanical energy storage positions which it may assume within the venous anatomy of a patient. The relative lengths of relatively flexible portions 4 and relatively stiff portions 2 may be varied according to the radii of the different venous curves which are anticipated to be encountered during lead implantation.

Thus, if it is anticipated that lead 10 will be implanted in a portion of the venous anatomy which is characterized by tightly curved venous portions, lead 10 may be configured to have relatively short stiff and flexible sections 2 and 4, respectively, to provide optimal results. Contrariwise, in the event the venous anatomy to be encountered during the implantation process is expected to be characterized by relatively gently curves, lead 10 may be configured such that relatively stiff sections 2 and relatively flexible section 4 have longer lengths to thereby provide optimal results. Lead 10 may also be appropriately configured such that portions 2 and 4 are of appropriate differing lengths for small, medium, and large radii curves encountered by the same lead 10.

It is important to note that when relatively stiff portion 2 of lead 10 is disposed in or along a curved section of the venous anatomy, an unstable mechanical equilibrium associated with a local maximum of stored potential mechanical energy being disposed in the curve results. It is therefore desired in the present invention that lead 10 have alternating relatively flexible sections 4 and relatively stiff sections 2 located within the venous anatomy in such a way that relatively flexible sections 4 are located in at least the major curves thereof.

The principle of varying the bending stiffness of lead 10 as a function of axial distance x may also be expanded to cover circumstances where the bending stiffness ($S_b$) is symmetric and equal around each axis of bending, or asymmetric and unequal around each axis of bending.

Figure 8B:
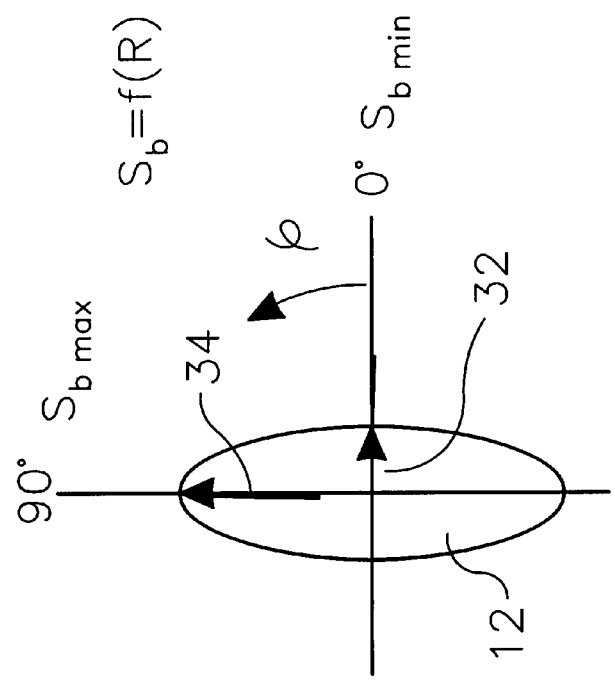
FIGS. 8A and 8B show two different embodiments of a lead body of the present invention in cross-section.
Figure 8A:
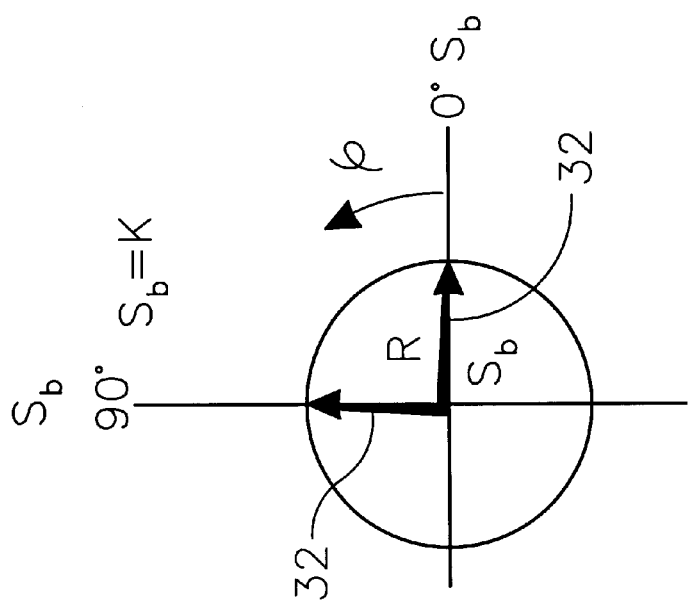

Referring now to FIGS. 8A and 8B, there are shown in cross-section lead body 12 exhibiting symmetric equal bending stiffnesses around each axis of bending in FIG. 8A and lead body 12 having asymmetric unequal bending stiffnesses around each axis of bending in FIG. 8B. Thus, lead 10 shown in FIG. 8A may be bent in any direction from 0° to 360° without any change in bending moment being required. Contrariwise, lead 10 shown in FIG. 8B requires more bending moment when lead 10 is bent in the directions of 0° and 180°, while less bending moment is required when lead 10 is bent in the 90° and 270° directions.

Figure 9B:
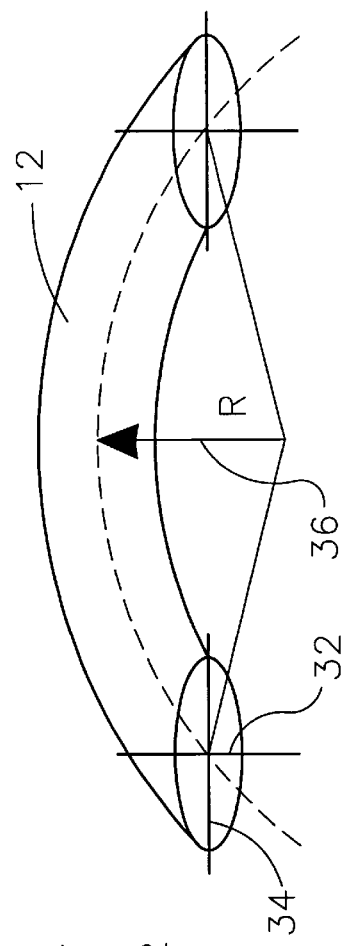
FIGS. 9A and 9B illustrate combined cross-sectional and perspective views of two different lead bodies of the present invention.
Figure 9A:
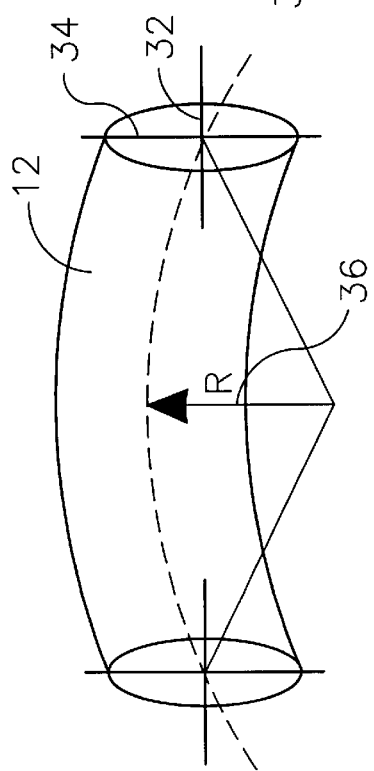

FIGS. 9A and 9B illustrate lead bodies which require asymmetric bending moments as a function of angular direction. In order to maintain minimal mechanical energy, lead body 12 illustrated in FIG. 9B will attempt to orient itself along the plane of the curve within which it is disposed such that bending preferentially occurs over the lead axis along the most flexible lead cross-section (e.g., the 90° and 270° orientations). This characteristic may be exploited so that lead body 12 may be oriented such that an electrode disposed along or near such a section exhibiting asymmetric bending stiffness is strategically placed within a vein. Thus, for example, a pacing or defibrillation electrode 14 disposed near such an asymmetric bending stiffness section may be oriented towards the myocardium (which may be beneficial in obtaining low pacing thresholds and improved sensing of signals).

FIG. 9A illustrates the natural orientation which the lead of FIG. 8B will assume within a curved portion of the venous anatomy. The lead configuration shown in FIG. 9B is one which requires maximum mechanical energy and therefore will not be assumed by lead 10 when disposed in a curved section of the venous anatomy.

Figure 10:
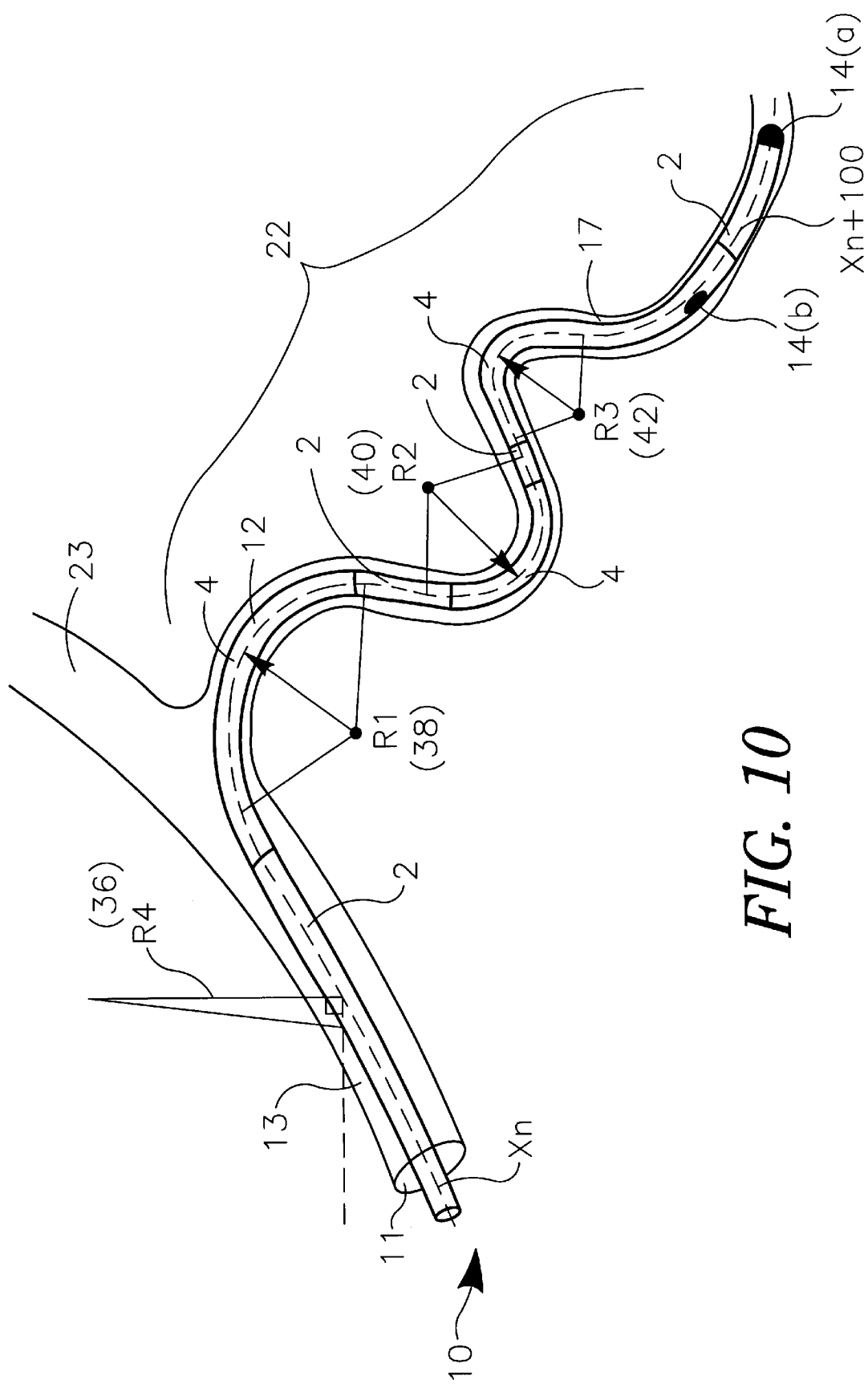
FIG. 10 illustrates an enlarged cross-sectional view of one embodiment of a lead of the present invention disposed within portions of the venous anatomy.

Referring now to FIG. 10, there is shown an enlarged cross-sectional view of lead 10 disposed within posterior cardiac vein 17 after having been routed through coronary sinus 13. FIG. 10 shows how venous vasculature exhibits curves having radii which alternate in direction and magnitude. Bending of lead body 12 along posterior cardiac vein 17 occurs substantially within a single plane (i.e. $R_1$, $R_2$ and $R_3$ are disposed substantially in the same plane). Because radii $R_1$, $R_2$ and $R_3$ are so much smaller than radius $R_4$, more radical bending of lead 10 is required in posterior cardiac vein 17. Bending of lead body 12 occurring along $R_4$ of coronary sinus 13 occurs in a plane which is approximately perpendicular to the plane along which $R_1$, $R_2$ and $R_3$ are disposed. Note that $R_4$ is substantially longer than $R_1$–$R_3$ and thus the curve of coronary sinus 13 is not only along a different plane but of substantially less magnitude. Consequently, a preferential orientation of lead 10 is determined principally by radii $R_1$–$R_3$ rather than by radius $R_4$. This, in turn, means that a lead having an asymmetric cross-sectional configuration or bending stiffness which varies asymmetrically as a function of cross-sectional angular position may be successfully employed to ensure the retention of lead 10 within a desired portion of the venous anatomy. For example, lead 10 may be configured to have a first asymmetric cross-sectional configuration for implantation along the distalmost portions of a selected cardiac vein in a first preferred orientation where bending radii are small, and to have a second asymmetric cross-sectional configuration for implantation in or along more proximally disposed portions of the venous anatomy and in a second preferred orientation, wherein the first and second orientations are different owing, for example, to the first and second cross-sections being angularly rotated in respect of one another.

Assuming the embodiment of the present invention illustrated in FIGS. 8B and 9A is employed for implantation within a desired portion of the venous anatomy, such a lead will have two orientations where stored mechanical energy will be achieved, namely at $\phi=90°$ or $\phi=270°$, assuming that the bending stiffness of the lead is equal in those opposite directions. Electrode 14(b) may be positioned on one side or the other of lead body 12 to stimulate a desired portion of the heart as shown in FIG. 10. Such positioning may be confirmed through the use of x-ray or echo identification of the orientation of electrode 14(b). If required, lead 10 may be rotated through 180° such that electrode 14(b) faces a desired direction.

Figure 11:
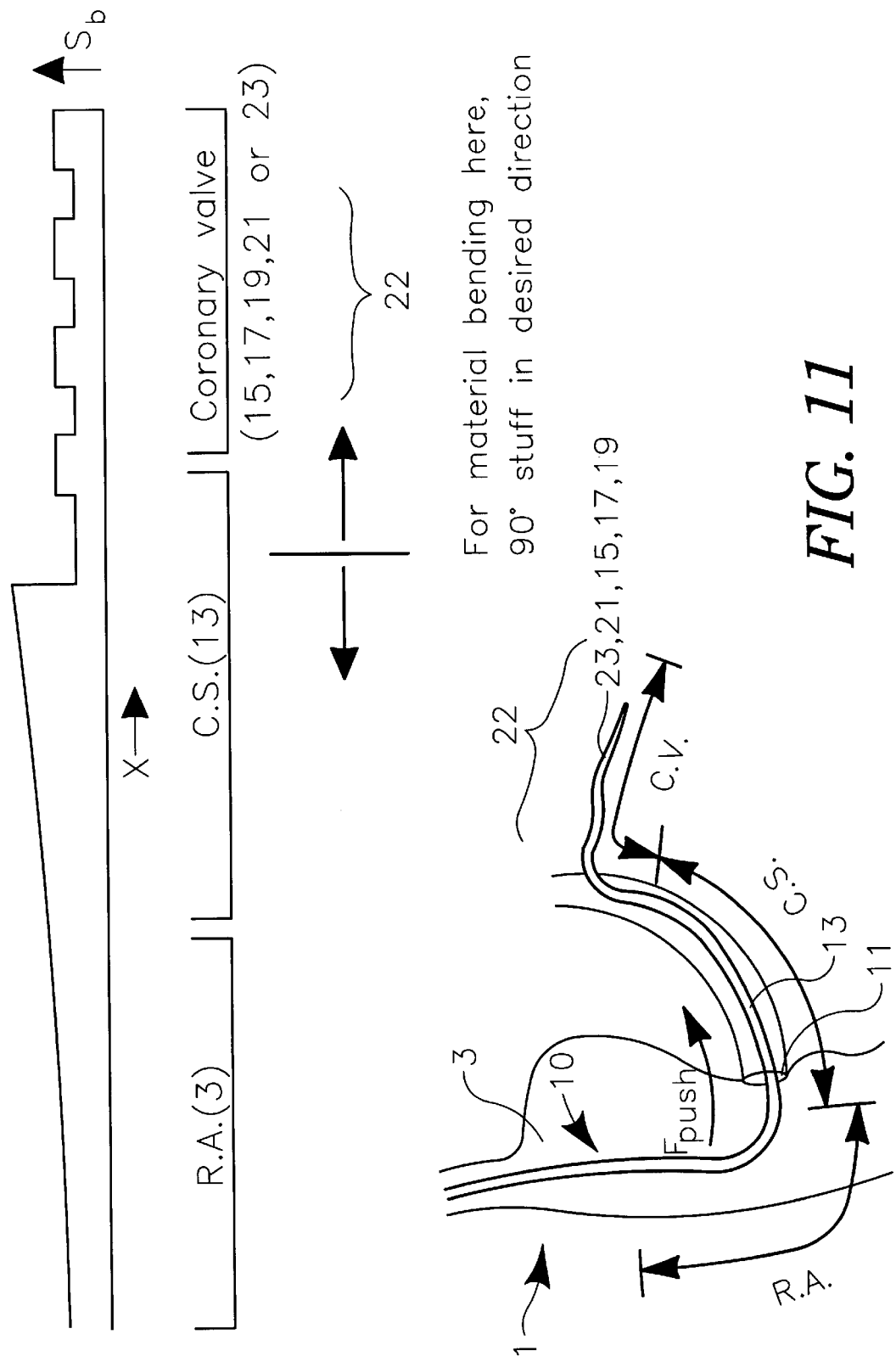
FIG. 11 illustrates one embodiment of the present invention adapted for implantation within various portions of the venous anatomy.

FIG. 11 illustrates another embodiment of the present invention, where lead 10 is adapted for implantation within right atrium 3, coronary sinus 13 and a selected cardiac vein. The distal tip 50 of lead 10 is disposed in the selected cardiac vein, while proximal therefrom a portion of lead 10 having bending stiffness characteristics which differ from those of the distalmost portions of lead 10. More particularly, and referring now to FIG. 11 again, it will be seen that distal portion 22 of lead 10 is characterized in having a bending stiffness profile which alternates between relatively stiff portions 2 and relatively flexible portions 4. Proximal from such sections of alternating relatively stiff and relatively flexible sections 2 and 4 there is disposed a section of lead body 12 in which bending stiffness increases in the distal direction, most preferably in the manner shown in FIG. 11. Note, however, that the increase in bending stiffness shown over those portions of lead 10 illustrated in FIG. 11 intended for implantation in right atrium 3, and optionally at least portions of coronary sinus 13, may increase monotonically, exponentially, step-wise or logrithmically. The important point is that bending stiffness over the portion of the lead implanted within the right atrium and optionally at least portions of the Coronary sinus have an increasing bending stiffness to create a force which will have a tendency to push the lead in the distal direction, even after implantation.

An outer layer or sleeve may surround lead body 12. Without any limitation intended, the sleeve may be constructed from a carbon coated silicone, steroid, steroid-eluting silicone, or a combination of silicone and an anti-fibrotic surface treatment element. Any of those compositions may help reduce tissue response to lead insertion so that lead 10 will not cause clots or adhere to the vessel wall, thereby allowing retraction of the lead in the future, if necessary. These compositions may also help prevent encapsulation of the electrode, thereby enhancing the effectiveness of the pacing and sensing capabilities.

One or more electrical conductors are disposed on or in lead body 12 and convey signals sensed by electrode 14 or permit the delivery of electrical pacing or defibrillation signals therethrough. Such conductors may be helically wound coils or multistrand twisted cables, ETFE coated, or fixed within a longitudinally disposed lumen of the lead body 12. The distal end of lead conductor 16 may be attached to electrode 14 while the proximal end thereof is attached to terminal pin 18 by crimping or laser weld means well known to those skilled in the art. Without any limitation intended, electrode 14 and terminal pin 18 may be manufactured from titanium or platinum-plated titanium. Conductor 16 preferably comprises electrically conductive braided or stranded wires. A lumen 30 may be formed within lead body 12 wherein a stylet of known construction may be positioned therein.

Figure 12:
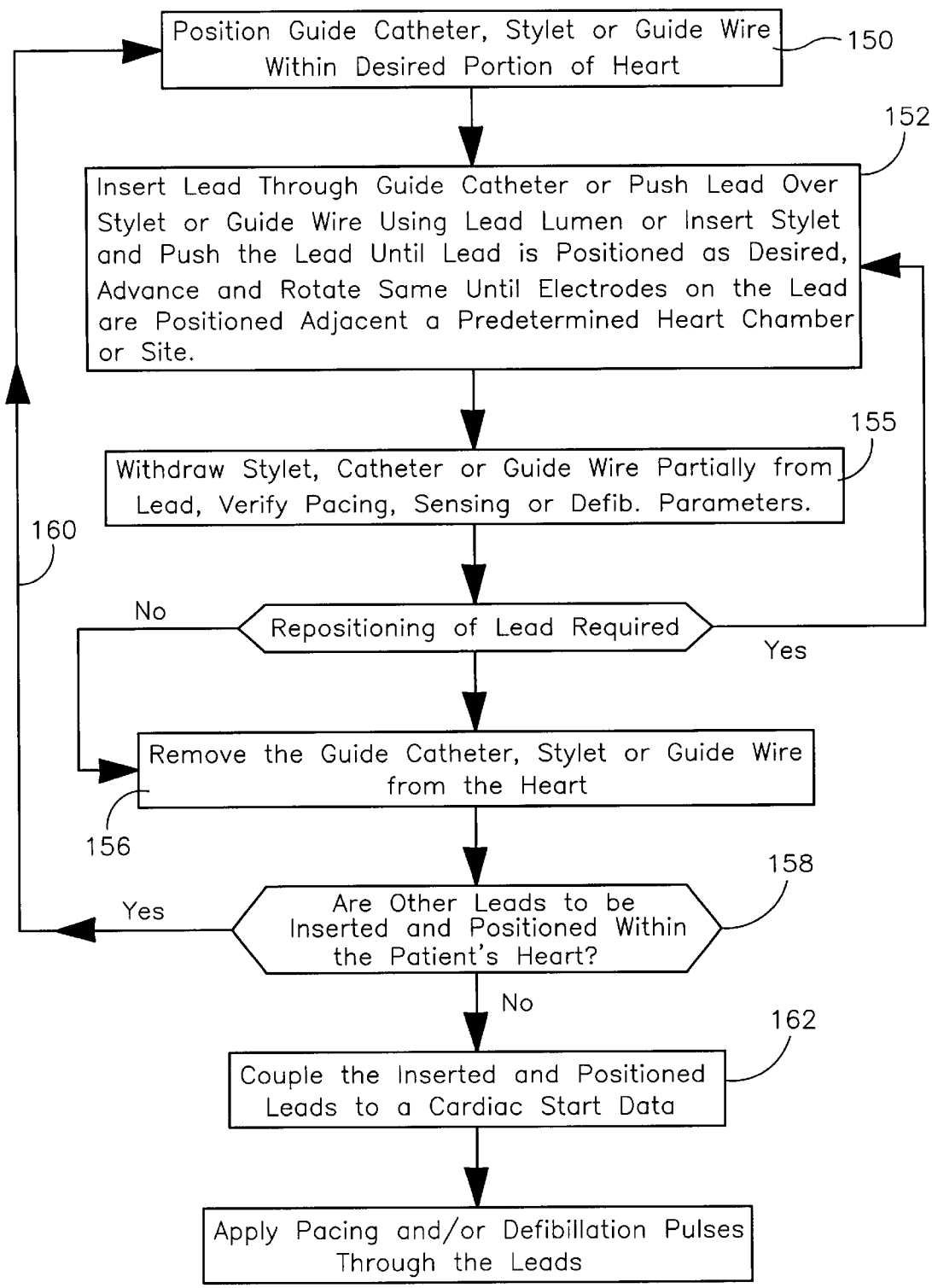
FIG. 12 illustrates several methods of implanting a lead of the present invention within a human heart and electrically stimulating same.

Having generally explained the features and positioning of lead 10, and referring now to the flow diagram of FIG. 12, some methods of pacing and/or defibrillating a patient's heart using a coronary vein lead 10 and implanting same will now be discussed. The method of pacing a patient's heart identified in the flow chart of FIG. 12 allows a user to effectively pace the left ventricle without increased risk of an ischemic episode.

The operator first positions a guide catheter of the tear away type known to those skilled in the art within coronary sinus 13 (block 150). Although the use of a guide catheter is not absolutely necessary, a guide catheter increases the ability of the operator to properly position lead 10 within a preselected coronary vein. Once the guide catheter has been positioned within coronary sinus 13, lead 10 is inserted through the lumen of the guide catheter and into a predetermined coronary vein under fluoroscopic observation (see Block 152). Lead 10 is positioned within the selected coronary vein, wherein the electrodes of lead 10 are aligned with the selected chambers to be paced. Those skilled in the art will appreciate that the electrodes may be constructed from a radiopaque material such that the position of the electrode is readily determined. After lead 10 is appropriately positioned in heart 1, the stylet or guide wire (if present) is removed from lead 10 (see block 154). The catheter is then removed from coronary sinus 13 (block 156) and the catheter is torn away as the catheter is pulled past the terminal pins of lead 10. Before removing the catheter from lead, however, electrical measurements may be taken. As noted above, a guide catheter may be used to direct a guide wire which is used to guide a support catheter to a desired position within a pre-selected coronary vein. The support catheter is then used to position lead 10 as described above.

After the guide catheter has been removed, the operator decides whether there are additional coronary vein leads to be inserted and positioned within the coronary veins of a patient's heart (see decision block 158). If other leads 10 are to be positioned within pre-selected coronary veins, then the above steps represented by blocks 150–156 are repeated (see loop 160). Those skilled in the art will appreciate that an additional lead of suitable construction could be positioned within the right atrium or ventricle. If no other leads 10 are to be inserted and positioned, then terminal pins 18 attached to each coronary vein lead 10 are coupled to corresponding terminal ports of cardiac stimulator 30 (block 162). Stimulator 30 is then programmed by known means to transmit a pacing and/or defibrillation pulse through each coupled lead 10 (block 164) to pace or defibrillate the pre-selected chamber of the patient's heart.

For placement of the lead tip in the atrial appendix a stylet is inserted and the lead pushed until the distal end of the lead is in the right atrium. The stylet is replaced with a J-shaped stylet to impart curvature on the distal end of the lead and to place the tip in the desired location of the right atrial appendix.

Once lead 10 of a suitable embodiment of the present invention has been inserted and positioned in heart 1, and without any limitation intended, the operator has the ability to, for example, pace or sense both the left atrium and left ventricle, or pace or sense the left atrium, left ventricle, and right atrium. When a separate right ventricular lead is positioned, pacing and/or sensing from all chambers of the heart may be possible. The diameter and construction of lead 10 provides the flexibility necessary to reduce substantially the likelihood that flexure of lead 10 will result in the coronary vein being eroded through. In this regard, the lead body 12 of lead 10 may be coated or impregnated with a biomedical steroid to reduce the inflammatory response of the coronary veins to the insertion and positioning of lead 10 therein. The selected biomedical steroid may also be used to reduce the amount of fiber build-up occurring between lead 10 and the coronary vein. Lead 10 may also be constructed to include an anchoring member such that lead 10 may be additionally anchored within the coronary vein or Coronary sinus.

Although specific embodiments of the invention have been set forth herein in some detail, it is to be understood that this has been done for the purposes of illustration only, and is not to be taken as a limitation on the scope of the invention as defined in the appended claims. Thus, the present invention may be carried out by using equipment and devices other than those described specifically herein. Various modifications, both as to the equipment and operating procedures, may be accomplished without departing from the scope of the invention itself. It is to be understood that various alternatives, substitutions and modifications may be made to the embodiment describe herein without departing from the spirit and scope of the appended claims.

In the claims, means-plus-function clauses are intended to cover the structures described herein as performing the recited function and not only structural equivalents but also equivalent structures. Thus, although surgical glue and a screw may not be structurally similar in that surgical glue employs chemical bonds to fasten biocompatible components together, whereas a screw employs a helical surface, in the environment of fastening means, surgical glue and a screw are equivalent structures.

All patents cited hereinabove are hereby incorporated by reference into the specification hereof, each in its respective entirety.

I claim:

1. An elongated implantable medical electrical lead for electrically stimulating a human heart or sensing electrical signals originating therefrom, comprising:

(a) a lead body having proximal and distal sections;

(b) at least one electrode for sensing or electrically stimulating the heart;

(c) a proximal end comprising an electrical connector, the electrical connector being contiguous with the proximal section of the lead body;

(d) a distal end contiguous with the distal section of the lead body;

(e) at least one electrical conductor having proximal and distal ends, the distal end of the conductor being operatively connected to the at least one electrode, the proximal end of the conductor being operatively connected to the electrical connector;

wherein the distal section of the lead body comprises at least first and second segments, the first segment having a bending stiffness $S_{bs}$ which exceeds the bending stiffness $S_{bf}$ of the second segment, the first and second segments being configured and dimensioned to impart a distally directed force to the distal end of the lead when the first and second segments are subjected to a bending moment resulting in a sufficient curvature of the distal section of the lead body and the lead body further comprises a first asymmetric cross-section configured for implantation in a first referred orientation in pre-determined distal-most portions of the heart's venous anatomy where bending radii are small, a second asymmetric cross-section configured for implantation in a second preferred orientation different from the first orientation in pre-determined portions of the heart's venous anatomy located proximal from the distal-most portions thereof.

2. The medical electrical lead of claim 1, wherein the bending stiffness of the distal section of the lead body increases distally in one of step-wise, monotonic, exponential or logarithmic fashion.

3. The medical electrical lead of claim 1, wherein the lead body has at least one pre-formed curve disposed therein.

4. The medical electrical lead of claim 1, wherein the distal section of the lead body is formed into a curved configuration.

5. The medical electrical lead of claim 1, wherein the bending stiffness of at least one of the first segment and the second segment is rotationally asymmetric.

6. The medical electrical lead of claim 5, wherein at least one electrode and the lead body are dimensioned and configured such that when the lead is appropriately implanted within a venous portion of the heart the rotationally asymmetric segment may be employed by a physician to orient placement of the at least one electrode such that the electrode is pressed against or directed towards a selected portion of the heart.

* * * * *